(12) United States Patent
Courtney et al.

(10) Patent No.: US 11,317,891 B2
(45) Date of Patent: May 3, 2022

(54) IMAGING PROBE WITH ROTATABLE CORE

(71) Applicants: SUNNYBROOK RESEARCH INSTITUTE, Toronto (CA); CONAVI MEDICAL INC., Toronto (CA)

(72) Inventors: Brian Courtney, Toronto (CA); Alan Soong, Etobicoke (CA); Deniz Jafari, Richmond Hill (CA)

(73) Assignees: CONAVI MEDICAL INC., Toronto (CA); SUNNYBROOK RESEARCH INSTITUTE, Toronto (CA)

( * ) Notice: Subject to any disclaimer, the term of this patent is extended or adjusted under 35 U.S.C. 154(b) by 550 days.

(21) Appl. No.: 16/080,225

(22) PCT Filed: Feb. 27, 2017

(86) PCT No.: PCT/CA2017/050248
§ 371 (c)(1),
(2) Date: Aug. 27, 2018

(87) PCT Pub. No.: WO2017/143457
PCT Pub. Date: Aug. 31, 2017

(65) Prior Publication Data
US 2019/0374196 A1    Dec. 12, 2019

Related U.S. Application Data

(60) Provisional application No. 62/300,583, filed on Feb. 26, 2016.

(51) Int. Cl.
*A61B 8/12* (2006.01)
*A61B 5/00* (2006.01)
(Continued)

(52) U.S. Cl.
CPC ............ *A61B 8/445* (2013.01); *A61B 5/0066* (2013.01); *A61B 5/0075* (2013.01);
(Continued)

(58) Field of Classification Search
CPC .................................................. A61M 25/0052
See application file for complete search history.

(56) References Cited

U.S. PATENT DOCUMENTS

| 4,142,592 | A | 3/1979 | Brusselmans |
| 4,794,931 | A | 1/1989 | Yock |
(Continued)

FOREIGN PATENT DOCUMENTS

| CA | 2941213 A1 | 7/2008 |
| CA | 2902668 A1 | 9/2014 |
(Continued)

OTHER PUBLICATIONS

Troughton, Handbook of Plastics Joining (Second Edition), Chapter 8—Laser Welding, pp. 81-95, William Andrew Publishing, 2009 (Year: 2009).*
(Continued)

*Primary Examiner* — Colin T. Sakamoto
(74) *Attorney, Agent, or Firm* — Hill & Schumacher

(57) ABSTRACT

The present disclosure provides for an imaging probe with a rotatable core which allows for rotating imaging assembly that is larger in diameter than the lumen in which the rotatable core resides, as well as methods to construct said probes. The imaging probes are generally elongate flexible imaging catheters for use in cardiovascular procedures. The ability to have a smaller lumen to hold the rotatable core simplifies the inclusion of other functional components to the catheter and may improve the quality of the images produced.

11 Claims, 9 Drawing Sheets

(51) Int. Cl.
*A61B 8/00* (2006.01)
*A61B 8/08* (2006.01)
*A61B 34/20* (2016.01)
*A61B 90/30* (2016.01)
*A61B 90/00* (2016.01)
*A61B 18/22* (2006.01)
*A61B 17/00* (2006.01)

(52) U.S. Cl.
CPC .......... *A61B 8/0891* (2013.01); *A61B 8/4254* (2013.01); *A61B 8/0841* (2013.01); *A61B 8/0883* (2013.01); *A61B 8/12* (2013.01); *A61B 18/22* (2013.01); *A61B 90/30* (2016.02); *A61B 2017/00526* (2013.01); *A61B 2034/2051* (2016.02); *A61B 2090/3614* (2016.02); *A61B 2090/3735* (2016.02)

(56) References Cited

U.S. PATENT DOCUMENTS

| | | | |
|---|---|---|---|
| 5,108,411 | A | 4/1992 | McKenzie |
| 5,178,150 | A | 1/1993 | Silverstein et al. |
| 5,373,845 | A | 12/1994 | Gardineer et al. |
| 5,569,221 | A | 10/1996 | Houser et al. |
| 5,596,991 | A | 1/1997 | Tanaka |
| 6,017,311 | A | 1/2000 | Sakamoto |
| 6,443,894 | B1 | 9/2002 | Sumanaweera et al. |
| 8,214,010 | B2 | 7/2012 | Courtney et al. |
| 8,303,509 | B2 | 11/2012 | Webler et al. |
| 8,317,711 | B2 | 11/2012 | Dala-Krishna |
| 8,712,506 | B2 | 4/2014 | Courtney et al. |
| 8,727,993 | B2 | 5/2014 | Lee et al. |
| 8,784,321 | B2 | 7/2014 | Courtney et al. |
| 8,821,376 | B2 * | 9/2014 | Tolkowsky ............ A61B 1/018 600/104 |
| 9,076,202 | B2 | 7/2015 | Courtney et al. |
| 2002/0082503 | A1 * | 6/2002 | Chandrasekaran ......................... A61B 18/1492 600/466 |
| 2005/0131445 | A1 * | 6/2005 | Holman ............... A61M 25/104 606/194 |
| 2006/0182907 | A1 * | 8/2006 | Atanasoska ........... A61M 25/10 428/34.1 |
| 2007/0260222 | A1 * | 11/2007 | Kraus ................ A61M 25/0014 604/527 |
| 2008/0188832 | A1 * | 8/2008 | Tanioka ............ A61M 25/0054 604/525 |
| 2009/0163915 | A1 * | 6/2009 | Potter ................ A61B 18/1492 606/41 |
| 2009/0264768 | A1 | 10/2009 | Courtney et al. |
| 2011/0319910 | A1 * | 12/2011 | Roelle .................... A61B 34/30 606/130 |
| 2013/0303920 | A1 * | 11/2013 | Corl ...................... B06B 1/0215 600/468 |
| 2017/0113018 | A1 * | 4/2017 | Shimizu ........... A61M 25/0052 |
| 2018/0125372 | A1 * | 5/2018 | Petroff ................. A61B 5/0084 |

FOREIGN PATENT DOCUMENTS

| | | |
|---|---|---|
| CN | 102563272 | 7/2012 |
| CN | 202469290 U | 10/2012 |
| JP | H7-155327 | 6/1995 |
| JP | 2003-52696 | 2/2003 |
| JP | 2007-530155 | 11/2007 |
| JP | 2011-507606 | 3/2011 |
| WO | 9013253 A1 | 11/1990 |
| WO | 2013077275 | 5/2013 |
| WO | 2013065473 | 10/2013 |

OTHER PUBLICATIONS

Lee et al., "A 10-Fr Ultrasound Catheter With Integrated Micromotor for 4-D Intracardiac Echocardiography", IEEE Trans. Ultra. Ferro. Freq. Con. 58, pp. 1478-1491 (2011).

Harm ten Hoff, "Scanning Mechanisms for Intravascular Ultrasound Imaging: a flexible approach", Thesis, Rotterdam, pp. 1-226 (1993).

International Search Report for related PCT application No. PCT/CA2017/050248, dated Jul. 25, 2017.

* cited by examiner

IMAGING PROBE WITH ROTATABLE CORE

CROSS-REFERENCE TO RELATED APPLICATION

This application is a National Phase application claiming the benefit of the international PCT Patent Application No. PCT/CA2017/050248, filed on Feb. 27, 2017, in English, which claims priority to U.S. Provisional Application No. 62/300,583, titled "IMAGING PROBE WITH ROTATABLE CORE" and filed on Feb. 26, 2016, the entire contents of which are incorporated herein by reference.

BACKGROUND

The present disclosure relates generally to the field of imaging probes for imaging mammalian tissues and structures using high resolution imaging, including high frequency ultrasound and optical coherence tomography.

Minimally invasive imaging of the body serves multiple purposes, including, for example, any of i) assessing tissue structures and anatomy; ii) planning and/or guiding interventions on localized regions of the body; and iii) assessing the result of interventions that alter the structure, composition or other properties of the localized region. Minimally invasive imaging, may refer to, for example, ultrasound and optical imaging methods. Minimally invasive ultrasound is very useful for intravascular and intracardiac procedures. For these applications, the ultrasound transducers are incorporated into a catheter or other device that can be inserted into the body. By way of example, two example implementations of minimally invasive ultrasound are intravascular ultrasound (IVUS), for imaging blood vessels, and intracardiac echocardiography (ICE) for imaging cardiac chambers. Both ICE and IVUS are minimally invasive, and involve placing one or more ultrasound transducers inside a blood vessel or cardiac chamber to take high quality images of these structures.

Optical imaging methods based on fiber optic technology used in the field of medicine include optical coherence tomography, angioscopy, near infrared spectroscopy, Raman spectroscopy and fluorescence spectroscopy. These modalities typically require the use of one or more optical fibers to transmit light energy along a shaft between an imaging site and an imaging detector. Optical coherence tomography is an optical analog of ultrasound, and provides imaging resolutions on the order of 1-30 microns, but does not penetrate as deeply into tissue as ultrasound in most cases. Fiber optics can also be used to deliver energy for therapeutic maneuvers such as laser ablation of tissue and photodynamic therapy. Additional forms of imaging related to this disclosure include angioscopy, endoscopy and other similar imaging mechanisms that involve imaging a site inside the patient using a probe to obtain images based on either the back reflection of light in the visible or infrared ranges of the spectrum. Further additional forms of high resolution imaging can use acoustic energy to create optical energy (sonoluminescence imaging) or optical energy to create acoustic energy (photoacoustic imaging).

Minimally invasive imaging has been implemented in many forms for assessing several different regions of mammalian anatomy, including the gastrointestinal system, the cardiovascular system (including coronary, peripheral and neurological vasculature), skin, eyes (including the retina), the genitourinary systems, breast tissue, liver tissue and many others. By way of example, imaging of the cardiovascular system with high frequency ultrasound or optical coherence tomography has been developed for assessing the structure and composition of arterial plaque. High resolution imaging has been used to measure vessel or plaque geometry, blood flow through diseased arteries and the effect of interventions on arterial plaque (such as by atherectomy, angioplasty and/or stenting). Attempts have also been made using high resolution imaging to identify vascular lesions that have not led to clinical symptoms, but are at increased risk of rupturing or eroding and causing an acute myocardial infarction. These so-called "vulnerable plaques" are an area of intense interest as the prospect of treating such plaques to pre-empt adverse clinical events is conceptually appealing. However, no particular imaging modality has as of yet demonstrated efficacy in this regard.

An area of increasing interest is the use of image guidance for procedures in structural heart disease and electrophysiology procedures. It is often necessary to place catheters within specific positions in the cardiac chambers in order to perform a therapeutic maneuver, such as the implantation of a device (such as a closure device for patent foramen ovales, valvular repair or replacement devices, left atrial appendage closure devices) or the placement of a therapeutic catheter (such as an ablation or cryotherapy catheter). It may also be necessary to guide intermediate steps in a procedure, such as crossing the atrial septum of the heart. The use of minimally invasive imaging can facilitate these steps.

The center frequency of minimally invasive ultrasound typically lies within the range of 3 to 100 MHz. Higher frequencies provide higher resolution but result in lesser signal penetration and thus a smaller field of view. Depth of penetration can range from less than a millimeter to several centimeters depending on several parameters such as center frequency and geometry of the transducer, the transducer's sensitivity, the attenuation of the media through which the imaging occurs and implementation-specific specifications that affect the signal to noise ratio of the system.

Optical coherence tomography generally has superior resolution to ultrasound and has the potential to better identify some structures or components in vascular and other tissues. It may also have better penetration than ultrasound through certain tissue components, such as calcified components. For example, fibrous cap thickness or the presence of inflammatory or necrotic regions near the surface of arteries may be better resolved with optical coherence tomography. However, optical coherence tomography is limited by its small penetration depth (on the order of 500 to 3000 microns) in most biologic media. Most such media are not optically transparent.

Angioscopy, endoscopy, bronchoscopy and many other imaging devices have been described which allow for the visualization of internal conduits and structures (such as vessels, gastrointestinal lumens and the pulmonary system) in mammalian bodies based on the principle of illuminating a region within the body near the distal end of a rigid or flexible shaft. Images are then created by either having a photodetector array (such as a CCD array) near the end of the shaft or by having a bundle of fiber optics transmit the received light from the distal end of the shaft to the proximal end where a photodetector array or other system that allows the operator to generate or look at an image representative of the illuminated region. Fiber bundles are bulky and reduce the flexibility of the shaft among other disadvantages.

Many of these imaging probes and flexible catheters rely on a rotatable conduit that extends through a lumen. The rotatable conduit is rotated by means of a rotational drive mechanism that is mechanically connectable or attached to the rotatable conduit's proximal end. One or more imaging assemblies reside attached to the rotatable conduit at a point remote from the proximal end of the rotatable conduit such that the imaging assemblies rotate in unison with the rotatable conduit. The imaging assembly may contain an emitter and/or receiver of imaging energy, such as an ultrasound transducer or optical emitter/receiver.

Minimally invasive devices typically have an elongate section that is designed to be advanced into the body. The elongate section is designed to be have a small maximal cross-sectional area so that the size of any surgical entry site or orifice through which the elongate section is advanced is minimized. This tends to minimize the risk of bleeding, discomfort, trauma and other aspects related to the insertion of the device into the body.

Catheters are used for diagnostic and/or treatment purposes and have variety of sensors and actuators mounted on them and/or embedded within their lumens. The catheter may be equipped with an imaging device employing an imaging modality such as optical imaging, optical spectroscopy, fluorescence, infrared cardiac endoscopy, acoustic imaging, photo-acoustic imaging, thermography, and magnetic resonance imaging. For example, an ultrasound or optical imaging device may be employed to locate and diagnose a diseased portion of the body, such as, a stenosed region of an artery. The catheter may also be provided with a therapeutic device, such as those used for performing interventional techniques including balloon angioplasty, laser ablation, rotational atherectomy, pacing, directional atherectomy and the like. In addition, catheters may be equipped with sensors such as electromagnetic position/orientation tracking sensors, temperature sensors, and force measurement sensors.

Intravascular catheters are required to have compact configuration in order to enable delivery into the vasculature. For example, catheters currently employed for intravascular ultrasound and intracardiac echocardiography are approximately 0.8 to 4 mm in diameter, where the smaller sizes of probes can be delivered more distally within the vascular tree of the coronary anatomy as the vessel caliber tapers down or as diseased vessels are stenosed. However, catheters equipped with an imaging assembly are also restricted in how small and compact they can be built, thus restricting the inner diameter of the distal end of the catheter.

Sections of the external sheath of a catheter are typically made out of one or more layers of biocompatible material, usually plastics, and may or may not be reinforced with a metallic or other braiding material. Most intravascular imaging catheters that rely on a rotatable conduit, such as a flexible torque cable, are assembled with an imaging core and an external sheath. The distal end of the external sheath may be closed, or more have a small opening in it to allow the efflux of air bubbles or other media when the inner core is flushed with a medium such as saline that allows the imaging energy to radiate out of the catheter with reduced losses and/or distortion. At the time of assembly, the distal end of the imaging assembly and rotatable conduit is advanced into the main lumen of the external sheath in a proximal to distal fashion. An imaging core comprises a rotatable conduit and an imaging assembly. A housing is coupled to the proximal end of the imaging core and is mechanically coupled in some way to the proximal end of the external sheath.

This method of assembly restricts the sheath to have a large enough inner cross-sectional area along the portion of the sheath that extends from the proximal entry site of its lumen to the final position along the long axis of the sheath at which the imaging assembly is destined to reside during operation. This in turn limits the size of the imaging assembly and the size of the ultrasound aperture to be small enough to fit within the inner lumen of the sheath in which the rotatable conduit resides.

The size of the inner lumen is limited to the outer size (i.e. outer diameter for a catheter with a circular cross-section, as is typically the case) less the portion of the cross-section occupied by the wall of the sheath. The wall must have a suitable thickness to provide the necessary mechanical performance for the catheter, as well as torquability, pushability, resistance to bursting when there is a pressure differential between the inner lumen and the surrounding environment (such as during flushing) and other similar mechanical features. The wall may be reinforced with reinforcement material, such as metal braiding or other materials known in the art.

Methods of bonding in the art of manufacturing catheters and other minimally invasive devices are several, including thermal bonding, laser welding, use of adhesives (including UV-cured adhesives) ultrasonic welding, press-fitting, fastening, using connectors and many others. Each have their own advantages and disadvantages. Among the techniques used for bonding of catheter sections, such as extrusions of thermoplastic polymers (Nylon, Pebax, Polyethylene and others), one of the preferred techniques is the use of thermal bonding. Thermal bonding two sections of a catheter together typically involves having a mandrel in some or all of the lumens of the two catheter sections, while placing a heat shrinkable polymer tubing over the catheter sections to be joined. Heat is then applied to the catheter to cause the heat shrink tubing to shrink while the polymeric materials of the catheter sections to soften and reflow, eventually causing the two sections to bond together. The mandrels preserve the integrity of those lumens that are subject to deform during the reflow process. The inner lining of the lumen may also have a liner, such as a PTFE liner.

SUMMARY

The present disclosure provides for an imaging probe with a rotatable core which allows for rotating imaging assembly that is larger in diameter than the lumen in which the rotatable core resides, as well as methods to construct said probes. The imaging probes are generally elongate flexible imaging catheters for use in cardiovascular procedures. The ability to have a smaller lumen to hold the rotatable core simplifies the inclusion of other functional components to the catheter and may improve the quality of the images produced.

In a first aspect, there is provided a method of assembling an imaging probe, the method comprising:

providing an elongate sheath having an inner lumen and a distal opening;

inserting, through the distal opening of the elongate sheath, a rotatable conduit having an imaging assembly connected to a distal end of the rotatable conduit, wherein a lateral extent of the imaging assembly is larger than a diameter of the inner lumen of the elongate sheath, such that upon insertion of the rotatable conduit into the inner lumen, the imaging assembly extends from the distal opening of the elongate sheath;

providing a distal tip having distal end and an open proximal end;

inserting the distal tip over the imaging assembly, such that the proximal portion of the distal tip contacts the elongate sheath over a contact region and preferably overlaps the elongate sheath over a contact region; and bonding the distal tip to the elongate sheath, wherein the bonding is performed via a local application of heat over the contact region.

In another aspect, there is provided an imaging probe comprising:

an elongate sheath having an inner lumen and a distal opening;

a rotatable conduit extending through said inner lumen, said rotatable conduit having an imaging assembly connected to a distal end thereof, wherein a lateral extent of said imaging assembly is larger than a diameter of said inner lumen of said elongate sheath, such said imaging assembly extends from the distal opening of said elongate sheath;

a distal tip housing said imaging assembly, wherein a proximal portion of the distal tip is bonded to a distal region of said elongate sheath and preferably overlaps a distal region of said elongate sheath.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. Unless otherwise specified, the terms "about" and "approximately" mean plus or minus 25 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

The present disclosure provides various example embodiments of medical probes having sheaths that have a larger inner diameter distal to a smaller inner diameter central lumen. The section with the larger inner diameter is remote from the proximal end of the sheath. In several example embodiments, the design is made possible by laser welding a distal tip to the distal end of a sheath or using localized thermal bonding with a heat shrink reflow process, in combination with a rigid reinforcement member in the catheter.

Figure 1:
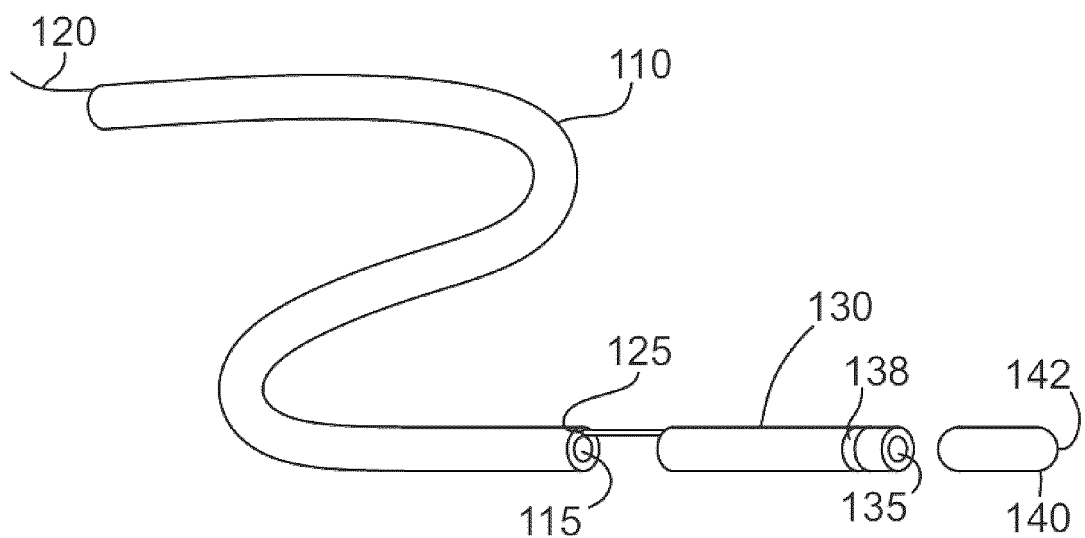
FIG. 1 shows the components of the sheath of an example medical probe.

FIG. 1 shows an exploded perspective view of several sections of a sheath of an example imaging probe 100 (e.g. a catheter) with a closed dome distal end and a deflectable tip. The elongate proximal section 110 has a main lumen 115, a generally circular cross section and a wall. There is a separate lumen 125 for a pull wire 120, which may have been constructed as is known in the art by including a separate piece of thin wall tubing, such as a polyimide tubing or as a multi-lumen extrusion. A softer distal section 130 with a generally softer material (relative to the proximal section 110) also has a main lumen 135 and a lumen for the pull wire 120. It also includes a pull ring 138, which is typically made of a metal and may have been included in the softer section by means of swaging or other processes known in the art. The pull wire 120 extends from the proximal end of the sheath, through the pull wire lumen 125 of the proximal section 110, through the pull wire lumen of the softer section 130 and is attached to the pull ring 138, such as by means of laser welding.

The distal tip 140 is terminated by a distal dome 142, and is formed from a material having properties suitable for allowing the transmission of imaging energy through the wall of the distal tip 140.

The distal tip 140 may be formed, for example, by a tip forming processes, a hot air station, or via injection molding. The material for the distal tip 140 may be selected for its properties such as mechanical strength, acoustic attenuation, optical clarity and others. The thickness of the wall of the distal tip 140 may also be designed with similar considerations.

Figure 2A:
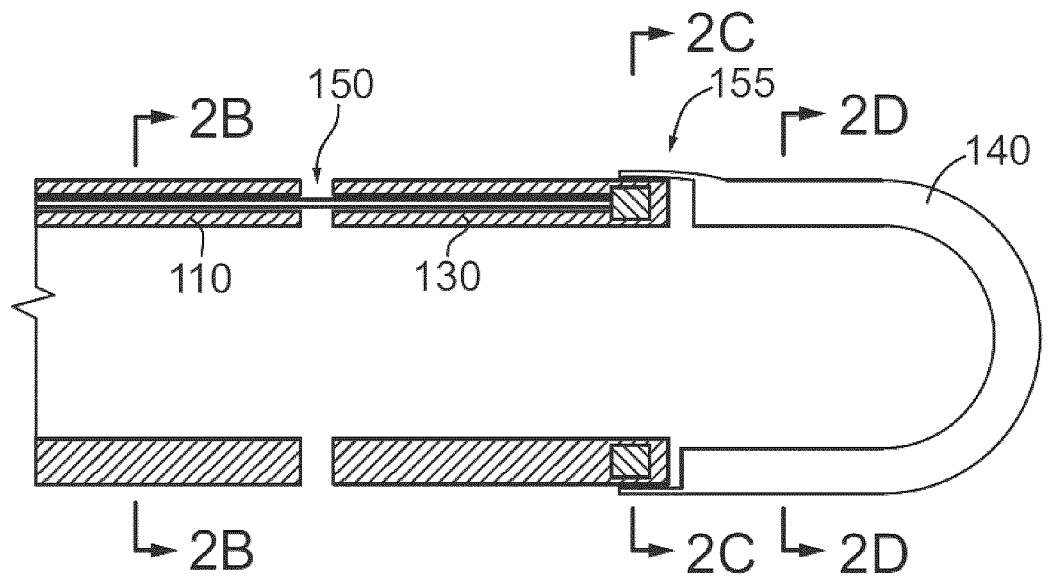
FIG. 2A shows a longitudinal sectional view of the probe sheath shown in FIG. 1, showing where the joints are formed when bonding the different portions of the probe sheath.
Figure 2B:
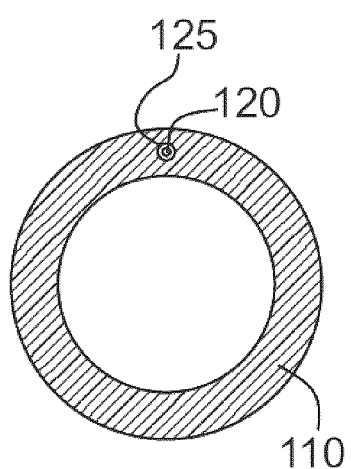
FIG. 2B shows a cross-sectional view of the probe sheath shown in FIG. 1, where the cross-section is taken through the elongate proximal portion of the sheath.
Figure 2C:
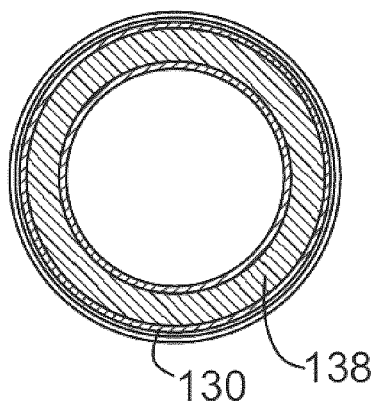
FIG. 2C shows a cross-sectional view of the probe sheath shown in FIG. 1, where the cross-section is taken through the softer distal portion of the sheath.
Figure 2D:
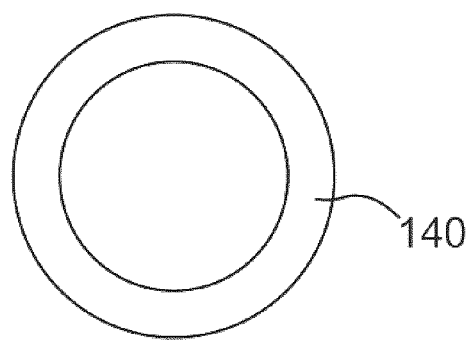
FIG. 2D shows a cross-sectional view of the probe sheath shown in FIG. 1, where the cross-section is taken through the distal tip portion of the sheath.

FIG. 2A shows a longitudinal sectional view of the walls of components of the sheath of the imaging probe 100 shown in FIG. 1, namely the elongate proximal section 110, the softer section 130 and the distal tip 140. FIG. 2B shows the cross-section of the elongate proximal section 110, while FIG. 2C shows the cross-section of the portion of the softer distal section 130 where the pull ring 138 resides, and FIG. 2D shows a cross-section of the proximal portion of the distal tip 140.

The various sections can then be joined together using a mandrel that occupies the main lumen of the three sections, including the hollow portion of the distal tip 140, placing a heat shrink around the assembly, applying heat in a controlled manner and then removing the mandrel and heat shrink. In FIG. 2A, a butt joint 150 is showing between the elongate proximal section 110 and the softer section 130. A lap joint 155 is showing between the softer section 130 and distal tip 140. Other orders of operation may be desirable in the construction of the catheter, such as joining the proximal 110, softer 130 and distal tip 140 sections in discrete steps, incorporating the pull wire lumen 125 after the proximal 110 and softer 130 sections have been joined or adding braiding and an outer jacket to the proximal 110 and softer 130 sections.

Figure 3A:
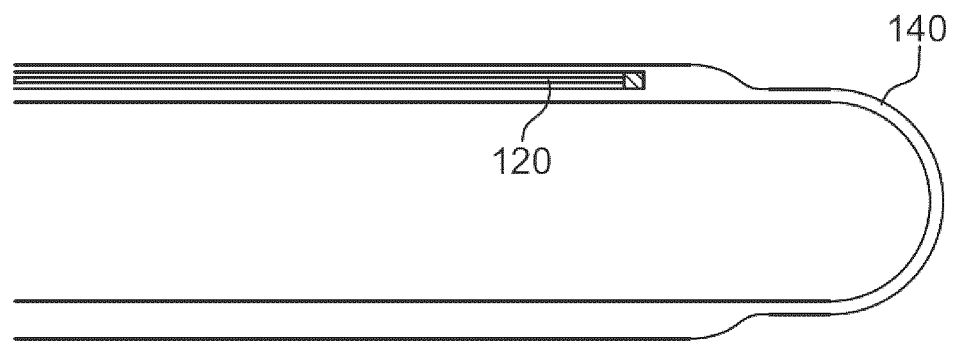
FIG. 3A shows a longitudinal sectional view of the probe sheath shown in FIG. 1, after bonding of the components of the sheath.

FIG. 3A shows the distal portion of the external sheath with a distal tip 140 and a pull wire 120 after the elongate proximal section, softer section and distal tip have been joined together at joints 155 and 150. If a user pulls on the proximal end of the pull wire 120 relative to the sheath, the side of the sheath on which the pull wire 120 resides will shorten and the softer section will deflect in that direction.

Figure 3B:
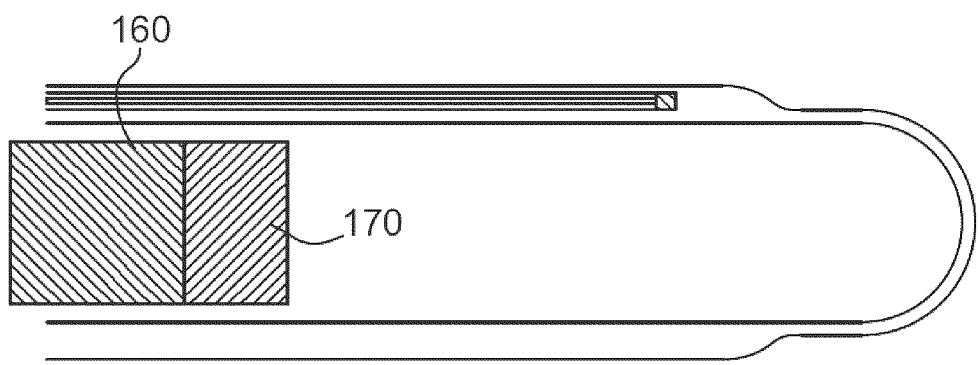
FIG. 3B shows a longitudinal sectional view of the probe sheath shown in FIG. 1, showing the introduction of an imaging assembly and an imaging conduit from the proximal direction/region.

FIG. 3B shows the advancement of a rotatable imaging conduit 160 (preferably a flexible torque cable) and a distal imaging assembly 170 (such as an ultrasound transducer) being advanced from the proximal end of the sheath towards the distal end. Examples of an imaging catheters with a rotatable imaging conduit can be found in US Patent Publication No. 20090264768, which is hereby incorporated by reference in its entirety.

Figure 3C:
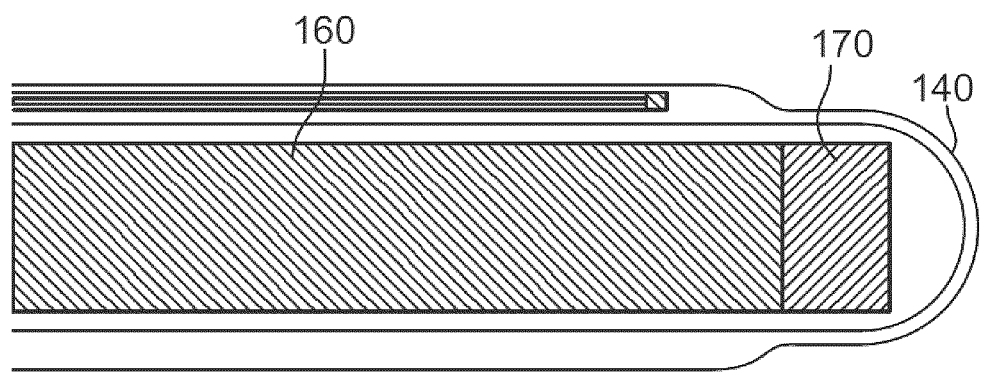
FIG. 3C shows a longitudinal sectional view of the probe sheath shown in FIG. 1, showing the imaging assembly residing at or near the distal tip.

FIG. 3C shows the position of the rotatable imaging conduit 170 when the imaging assembly 170 is aligned with the distal tip 140, which acts as an imaging window for imaging energy, such as ultrasound waves or light, to travel between the imaging assembly 170 and a region exterior to the distal tip 140 of the catheter.

While it is desirable to minimize the cross-sectional area of the elongate section in order to be as minimally invasive as possible, it is in many cases desirable to maximize the size of a functional component within the device, such as an ultrasound transducer. A larger aperture ultrasound transducer tends to be more sensitive than a smaller aperture transducer. Furthermore, the ultrasound beam of a transducer tends to be better focused over a longer axial distance (i.e. along the axis of propagation of the ultrasound) with larger aperture sizes.

Furthermore, when using thermal processes to bond catheter components together, such as laser welding, ultrasonic welding, or application of heat via convection, conduction, or radiation, it is important to avoid causing undesired damage to nearby components of the catheter. In imaging catheters, such as those with complex scanning mechanisms as disclosed in US Patent Publication No. 20090264768, several components of the imaging assembly may be sensitive to excessive heat, such as the insulation on electrical conductors, coatings, plastic housing components, epoxies, the imaging tip which often has a thin wall or other adhesive used in the assembly of the scanning mechanism etc.

Figure 4:
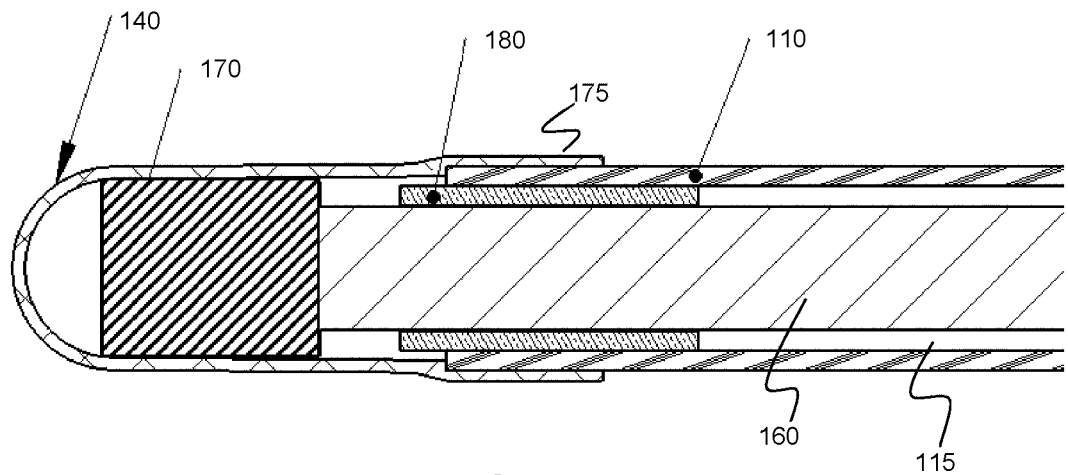
FIG. 4 shows an example embodiment of an imaging probe in which the radial extent of a distal imaging assembly is larger than the inner radius of the elongate proximal sheath, where the distal tip is bonded to the elongate proximal sheath while being mechanically supported by a rigid reinforcing member.

An example embodiment of imaging catheter with an imaging assembly that addresses these problems is shown in FIG. 4. The imaging assembly 170 is larger than the proximal section as shown in FIG. 4 and includes an imaging assembly 170 at the tip of the catheter that has a larger diameter than the main lumen 115 of the proximal section 110 attached to it. It is noted that the example embodiment shown in FIG. 4 shows an elongate proximal portion 110 bonded to the distal tip 140. It will be understood that the distal tip may instead be bonded to an intermediate sheath portion, as shown as the softer intermediate sheath portion in FIGS. 2-C and FIGS. 3A-C. The proximal sheath portion 110 may be made of a polyethylene extrusion, as well as distal tip 140, although any other medically graded plastics may alternatively be employed, provided that the two plastic extrusions are compatible with each other and can form a strong bond. The imaging assembly may be fully or partially rotatable.

In one example method of assembling the imaging catheter shown in FIG. 4, the imaging assembly 170 and rotatable imaging conduit 160, along with electrical leads, fiber optics, flush lumens and other components that reside within the portion of the rotatable imaging conduit 160 are inserted from the distal end of the sheath before the distal tip 140 is attached. Distal tip 140 is then placed on the proximal sheath portion 110 and the two plastics are bonded on the overlapped section 175 which is on top of a rigid reinforcing member 180. In some example implementations, the rigid reinforcing member 180 may serve a dual purpose of the catheter design, such as the pull ring for a deflection mechanism and/or a marker band.

In one example implementation, the distal tip 140 is bonded to the proximal sheath portion 110 using heat shrink and the local application of heat. The rigid reinforcing member 180 acts in a manner similar to a mandrel by providing an outer radial force in the region 175 where the distal tip 140 and the proximal sheath portion 110 are compressed together by the heat shrink, which provides an inner radial force. The rigid reinforcing member 180 may be a separate hollow cylinder solely provided for this purpose. Low temperature heat shrink may be employed, where the low temperature heat shrink has a composition that shrinks at lower temperatures than the melting point of the plastic material forming the proximal sheath portion 110. For example, polyolefin heat shrink tubing can be activated at approximately 90 degrees C. compared to the melting temperature of Pebax 7233 that has a melting point of approximately 175 degrees Celsius. The heat shrink provides enough pressure to hold the entire assembly together. This process is not limited to the use of heat shrinks. Other instruments such as, but not limited to, a radial band, precision clamp, or other fixtures, can be used. Clear materials that pass laser energy therethrough can be used. Alternatively, other means of bonding regions may employed. Regions can be bonded using adhesives, such as cyanoacrylates, or various epoxies. Regions call also be joined with mechanical approaches such as press-fits, retaining pins or clips, etc.

Alternatively, the overlapping region of the distal tip 140 and the proximal sheath portion 110 may be laser welded together, whereby the laser energy is localized to the joint region 175 such that the there is no collateral damage to the neighbouring parts of the catheter. In one example embodiment involving laser welding, in which the distal tip is at least partially transparent, a light absorbing material may be applied between the portions of the distal tip 140 and proximal sheath portion 110 that are to be joined together, in order to enhance the localization of the absorption of the light and thus localize the heat produced. In one example implementation, the dome tip 140 is held in contact with the distal end of the sheath by heat shrink that allows the laser energy to pass therethrough. This process is not limited to the use of heat shrinks, and other instruments, such as a clear radial band, precision clear clamp made of glass or a polymer compatible with the laser energy or other fixtures that would pass the laser energy therethrough can be used.

For example, in one example implementation in which optically transparent polyethylene extrusions are employed to form the proximal sheath portion 110 and the distal tip 140, a light absorbing material (Clearweld® Solution Pen LD220C) may be used to absorb laser radiation from a YAG laser beam that passes through the top clear layer of plastic and produce heat at the intersection of the two plastic parts, thereby melting the plastic locally and bonding the two sections together. Although the example fabrication method described above employs a YAG welding laser, the present example process is not limited to utilizing a laser welder only. Other methods for bonding the joints with different inner diameters are for example using a focused hot air station that doesn't spread the heat much along the sheath, or using a hot iron, or other type of lasers such as diode lasers.

Other example alternatives to the aforementioned method include using colored thermoplastic extrusions, or the use of suitable additives or pigments to the transparent plastics, such as carbon black.

The rigid reinforcement member 180 can be used to provide structural support if the laser welding approach does not adequately localize the heat generated. Alternatively, the laser welding method may be performed in the absence of a rigid reinforcing member if the application of heat is adequately localized to the interface between distal 140 and proximal sheath portion 110.

Figure 5:
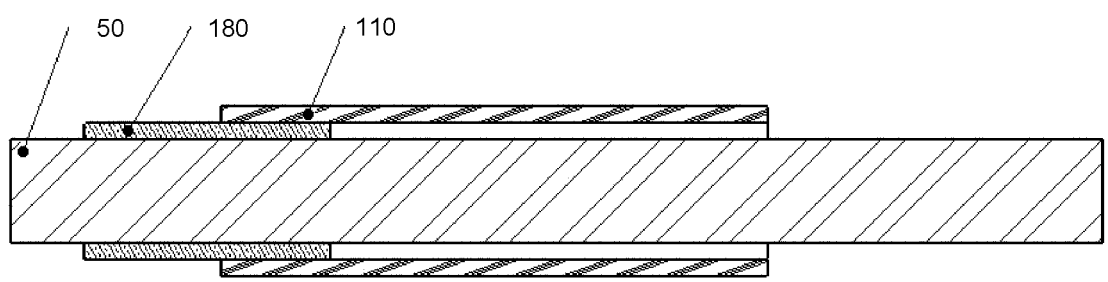
FIG. 5 illustrates the use of a mandrel when bonding the elongate proximal sheath to the rigid support member, prior to the bonding of the distal tip.

FIG. 5 shows an example embodiment in which a rigid reinforcement member 180 is placed over a mandrel 50, and where one end of a plastic extrusion is placed over the rigid reinforcement member 180. According to one example joining method, heat shrink is then placed on top of the assembly. A hot air station is used to melt the plastic extrusion 110 on top of the rigid reinforcement member 180. This results in a thin layer of plastic to cover a portion of the rigid reinforcement member 180 and to hold it in place at the distal end of the sheath. The heat shrink is then peeled off and the mandrel 50 is removed.

A light-absorbing (e.g. Clearweld®) solution is then applied to the outer surface of the plastic sheath 110, on the portion that is on the rigid reinforcement member 180. The solution is given few minutes to dry. The proximal end of distal tip 140 is then placed on top of the rigid reinforcement member 180 and the distal end of extrusion 110, such that the overlapped section of the sheath 110 and the distal tip 140 are adequately overlap with the applied light absorbing solution. Alternatively, an overlapped bond could be made by having the distal end of the proximal section 110 on the outside layer and the proximal end of the distal tip 140 inside the distal end of the proximal section 110. The laser radiation is directed onto the overlapped section to bond the two layers. The laser beam passes through the first transparent layer and is absorbed at the intersection of the joint components, generating localized heat in return and creating an effective and reliable thermal bond. In one example implementation, the overlapped section of the two plastic layers is located at or near the middle of the rigid reinforcement member 180, since directing a laser at the edge of the rigid reinforcement member 180 may result in melting and deformation of section of the plastic that is not supported by the rigid reinforcement member 180.

In one example implementation, this example process facilitates the fabrication of a catheter having a rotatable imaging conduit supporting an imaging assembly, where the imaging assembly is housed at or near the distal end of the catheter, and where the imaging assembly has a cross-sectional shape and size that is larger than what the lumen of the sheath would have otherwise accommodated by inserting the imaging assembly into the catheter sheath in a proximal to distal fashion. By enabling the attachment of the distal tip to the sheath as a step that occurs after the imaging assembly and rotatable conduit are placed in their functional location within the portion of the sheath that is to be inserted into the body (i.e. the portion whose cross-sectional area is minimized to minimize trauma to the body), the imaging assembly can have a larger size than it otherwise would have according to the conventional proximal-to-distal insertion method.

In another example implementation, the wall of the sheath proximal to the distal tip can be made thicker and therefore can be made to include more functional components, as will be explained later.

In one example embodiment, the distal section of the sheath may not need a separate rigid reinforcement member, as the sheath may have a thick enough wall thickness to withstand any inward radial forces applied by the heat shrink, and may also be thick enough to dissipate any localized heat used to create the thermal bond between the distal tip and section of the sheath 110 thus preventing the heat from deforming or otherwise damaging the catheter or its internal components.

In the examples shown in FIGS. 1, 2A-D and 3A-C, a pull wire and pull ring were included as components of the catheter to demonstrate that the inclusion of a feature such as a pull wire lumen along the elongate portion of the catheter requires space within the overall area of the cross-section of the elongate portion, thus limiting the size of the main lumen, and in turn, limiting the radial extent (size and shape) of an imaging assembly that is housed within the main lumen. However, many example embodiments of the present disclosure do not constrain the radial extent of the imaging assembly even in the presence of a pull-wire lumen. For example, the cross section of the imaging portion of the distal tip may be designed to be larger than the cross-section of the main lumen by virtue of having a thinner wall thickness in the distal tip (for better imaging properties) than the wall surrounding the main lumen for of ease of manufacture, cost and/or structural integrity of the elongate portions of the catheter, such as the proximal elongate portion and the softer portion as in the exemplary embodiment.

As was mentioned previously, it may be desirable to have as large a diameter (radial extent; size and shape) as possible for the imaging assembly to improve functionality and/or image quality. In the case of ultrasound imaging, the imaging assembly may include more than an ultrasound transducer. For example, the ultrasound transducer may be mounted on a housing and pivot assembly that allows the ultrasound transducer to pivot around a tilt access to enable 3D imaging, as disclosed in US Patent Publication No. 20090264768. A 3D forward looking scanning mechanism may benefit from additional space in the distal tip of the catheter for the imaging assembly, where the additional space be used, for example, to accommodate a larger imaging assembly, which may then be used to make more room for components of the imaging assembly, including by not limited to a potentially larger ultrasound transducer than may otherwise be accommodated. The 3D scanning mechanism would preferably, but not necessarily, be located near the distal end of the catheter so that there is a relatively unobstructed line of sight free through the dome shaped imaging window, especially when the beam is emitted in a more forward-looking direction.

The example methods of the present disclosure that permit the imaging assembly to be inserted from the distal end, allows the catheter be configured to have smaller inner lumen along its sheath. Such a smaller central lumen would allow for thicker wall diameter. This additional space may be employed, for example, to add off-centered lumens within the sheath.

One example use of additional side lumens is the incorporation of additional pull wires that allow better maneuvering of the catheter. Maneuverability of catheters is especially important for ablation procedures, where the catheter is used to burn specific abnormal heart tissues that are arrhythmogenic sites within the atria and ventricles. In case of imaging catheters, this extra maneuverability allows for greater control of the field of view. Another use of side lumen is possibility of adding one or more flush lumens and/or one or more other fluid delivery lumens to the catheter.

The additional cross-section space in the sheath that is made available by employing a central lumen that has a diameter this less than the lateral extent of the imaging assembly (or other distal functional device or element) can also or alternatively be used to insert or otherwise incorporate additional sensors into the catheter that are isolated from the central lumen, such as, but not limited to, temperature sensors, electromagnetic sensors for electro-anatomical mapping, fiber optics for rotary encoders (particularly synergistic as the reduced diameter of the torque cable might make the imaging system more susceptible to NURD) or pass through isolated wires attached to electrodes used for sensing intracardiac electrograms and/or cardiac pacing.

Accordingly, additional functionality could be added to either a 2D or 3D imaging catheter by including at least a portion of one or more of the following function enhancing components in the catheter sheath:

1. the addition of one or more pose sensors or emitters, such as those provided by Northern Digital (NDI) or Ascencion Technology to provide the ability to sense the position and/or orientation of a distal section of the catheter;
2. the addition of a rotary encoder (such as one or more of those described in U.S. Pat. No. 8,712,506, which is herein incorporated by reference in its entirety);
3. the addition of one or more fiber optic based sensors, such as a Bragg grating, an optical pressure sensor or optical temperature sensor;
4. the addition of one or more pacing or electrocardiogram (ECG) electrodes;
5. one or more deflection mechanisms (e.g. pull wires) to add more steerability to the sheath, such a bidirectional steering;
6. the addition of an accessory lumen that has exit ports both proximally and delivery for fluid delivery or delivery of a separate device (such as a wire) to the region of the anatomy surrounding the distal portion of the catheter;
7. additional flushing or venting lumens that are in fluid communication with an interior region of the catheter to help improve image quality, such as by removing air from the distal region that can interfere with imaging; and/or
8. the addition of wiring for the inclusion of an electromagnetic winding near the tip, such as one to enhance the tilting performance of a magnet-based scanning mechanism or to sense electromagnetic signals, such as electromagnetic (EM) noise that might be interfere with image quality.

It is noted that the addition of many of these function-enhancing components may be preferred if the distalmost portion of the function-enhancing component is located proximal to the imaging assembly along the long (longitudinal) axis of the catheter. For example, wires, fibers, and/or lumens used to enable the functionality of these components may interfere to a minimal or significant extent with the imaging performed by the imaging assembly if they were to cross the field of view of the imaging assembly. For example, wires can cause shadowing in ultrasound imaging, so the aforementioned embodiments may be preferred for the case of ultrasound, but it may not be necessary for a pacing electrode and its associated wire to be located proximal to the imaging assembly.

Figure 6A:
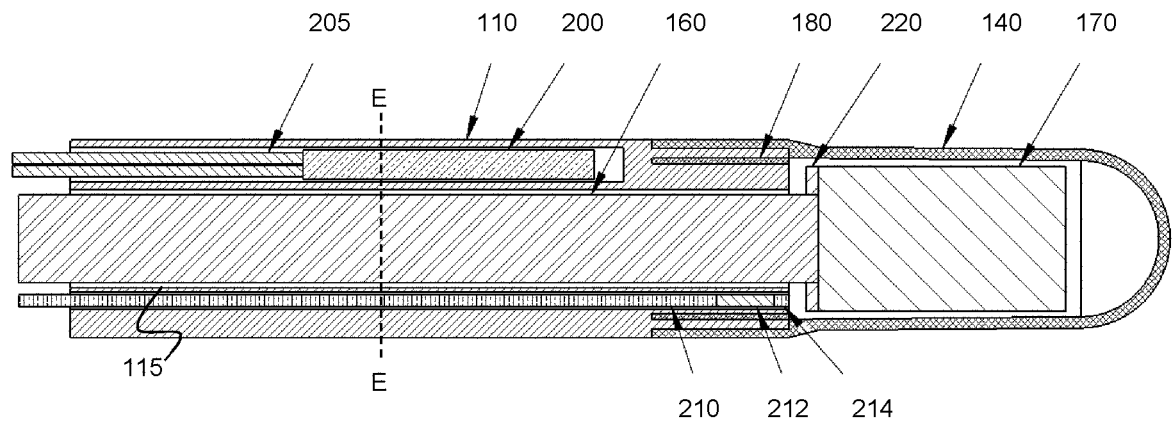
FIG. 6A illustrates an example embodiment of an imaging probe in which the radial extent of a distal imaging assembly is larger than the inner radius of the elongate proximal sheath, and wherein the elongate proximal sheath includes a pose sensor and a fiber optic that is in optical communication with a rotary encoder interface.
Figure 6B:
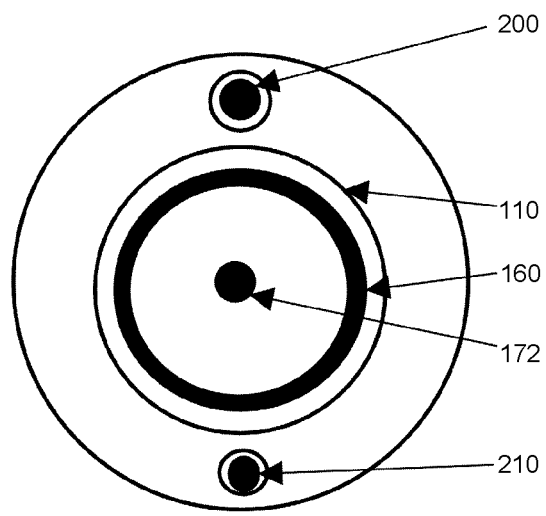
FIG. 6B shows a cross-section through the line E-E shown in FIG. 6A.
Figure 7:
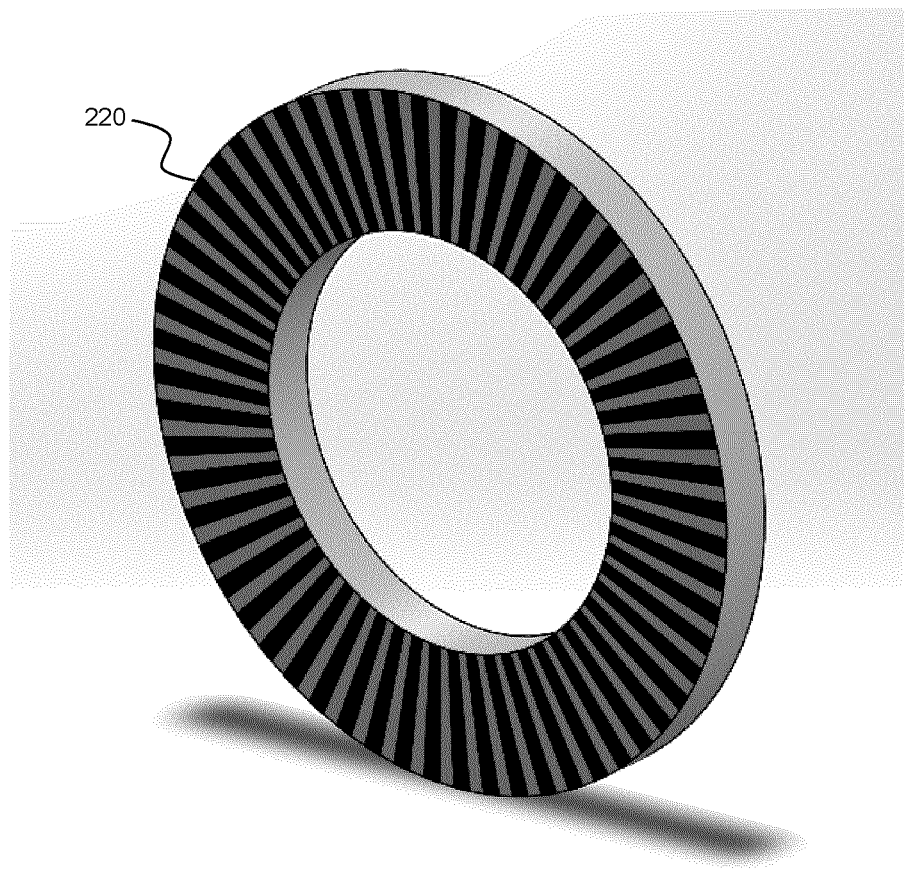
FIG. 7 shows an example rotary encoder substrate of a rotary encoder mechanism.

As an example, FIGS. 6A and 6B show a distal section of the catheter that includes both a pose sensor 200 within the wall of sheath 110, wired electrically conductive conduits 205, torque cable (rotatable imaging conduit) 160, imaging distal tip 140, imaging assembly 170 and structurally rigid member 180. In FIGS. 6A and 6B, the structurally rigid member 180 is shown embedded in sheath 110, but in other example implementations (see, for example, FIG. 4), the structurally rigid member 180 can contact an inner surface of the sheath 110. Also included to provide rotational encoding capabilities are fiber optic 210, optional imaging spacer 212 and optional lens 214 incorporated into the sheath, as well as encoding substrate 220 that rotates in unison with a rotating component such as the imaging assembly 170. A perspective view of the encoding substrate 220 is shown in FIG. 7. The central circle in FIG. 6B shows an electrical coaxial cable 172 for delivering an ultrasound signal to and from the imaging assembly 170.

It is noted that a synergistic effect may be achieved by combining a smaller torque cable with a rotary encoder for detecting rotational motion. A smaller main lumen and smaller torque cable generally tends to negatively impact the rotational performance of the torque cable in terms of how closely the rotation of the proximal end of the torque cable translates into an equal amount of rotation of the distal end. However, a rotary encoder reduces the need for one-to-one transmission along the length of the torque cable. This relieves several design constraints of the rotating conduit and may allow a smaller and/or simpler design of torque cable, or even substitution of the torque cable with a simpler structure, such as a hollow polymer extrusion. Therefore, the rotary encoder enables a smaller diameter and potentially simpler torque transmission means, which in turn provides space within the wall of the catheter for the rotary encoder to be included in the catheter design.

The pose sensor 200 (or pose emitter) may be, for example, one of those known in the art such as those supplied by NDI, Ascension Technology, or as found in a Carto system (Biosense Webster). The advantage of including a pose sensor/emitter with an imaging catheter is well known in the art, as it provides coordinates within a reference coordinate system (typically a coordinate system that is referenced to a home position relative to a patient or the table on which the patient lies) as to where the images are being collected. For example, U.S. Pat. No. 6,443,894 provides an example of an imaging catheter that includes a pose sensor.

Pose sensors have previously been incorporated onto array-based intracardiac echocardiography (ICE) catheters, where there is no rotational torque cable or rotary motor. Furthermore, the position and orientation of the images relative to the position and orientation of the pose sensor are more easily determined with an array-based imaging catheter, as there is a rather fixed geometric relationship between the pose sensor and the imaging array transducer. In a mechanical imaging catheter, the imaging transducer changes its position or orientation relative to the pose sensor. Therefore, in order to map the images from the imaging assembly onto the pose sensor reference frame, it is helpful to have a method of detecting the position and/or orientation of the imaging transducer. In its simplest form, a rotary encoder located external to the patient, coupled to a proximal portion of the torque cable (such as the rotary encoder in the patient interface module), provides some information about the rotational position of the imaging assembly. However, the precision of an external rotary encoder relative to the true rotational orientation within the sheath may not be accurate due to imprecision of the torque transmission provided by the torque cable, as it is an elongate and imperfect component that can be subject to artifacts such as non-uniform rotational distortion. Furthermore, in some embodiments of imaging catheters, the sheath in which the pose sensor is incorporated may be able to rotate freely relative to the rotating components within the catheter. Furthermore, in some embodiments, such as a 3D imaging catheter, the imaging assembly may be configured such that the angle at which the imaging beam is emitted is tiltable into more forward or side viewing directions, and there may be a tilt angle encoder provided, such as those described in US Patent Application Publication No. 20120197113.

To augment the ability to map the imaging data (such as complete image frames, imaging vectors or imaging pixel samples) from an image coordinate system to a pose sensor reference coordinate system, it may be desirable to incorporate a rotational encoder 220 between the imaging assembly and the sheath, such as that included in FIG. 6A. It may similarly be desirable to incorporate a tilt angle encoder within the imaging assembly or sheath, such as those described in US Patent Application Publication No. 20120197113 and U.S. Pat. No. 8,712,506.

A magnet-based pose emitter located on a rotational IVUS catheter has been built by Mediguide (owned by St. Jude), where there is a small magnet placed on the tip of an IVUS catheter to enable sensing of the position of the IVUS catheter tip. The Mediguide magnet does not require wires along the length of the catheter, and therefore there is no imaging artifact created by the addition of a Mediguide magnet to the catheter tip from any wires that would normally be associated with several other embodiments of a pose sensor or emitter.

NDI supplies pose sensors that are less than 1 mm in diameter and less than a centimeter in length that can detect the position and orientation in either 5 or 6 degrees of freedom. Such pose sensors can enable the detection of the 3D position within a reference coordinate system (e.g. x,y,z), as well as two or 3 angular orientations of the sensor. The roll axis of the orientation (e.g. rotational orientation around an axis of the sensor, such as the long axis of the sensor) is provided by a 6 degree of freedom sensor, but not a 5 degree of freedom sensor.

The NDI system works by having a field generator placed near the patient that creates an electromagnetic field over the patient. The sensor includes one or more coils and associated wiring that detect the local electromagnetic field and transmit the signal(s) to a console along the associated wiring to a processing unit to determine the position and/or orientation of the sensor. The field may be either a static magnetic field or a time-varying electromagnetic field. A commonly used system employs a time-varying electromagnetic field to achieve position and orientation sensing.

Another form of position sensing involves the use of electric impedance measurement through the body to triangulate the position of an electrode that is in contact with the anatomy. This system usually has two or more (usually at least three) reference electrodes or electrode patches attached to the body from which the catheter electrode positions are triangulated or otherwise estimated.

It is also possible to use two impedance-based position sensors along the length of a catheter (i.e. electrodes) to obtain two sets of xyz coordinates, which can be employed to provide information pertaining to two degrees of orientation.

Similarly, two sensors, where one sensor has five degree-of-freedom (DOF) sensing and the other sensor has at least position sensing at roughly the same longitudinal position on the catheter can be employed to provide the information needed to determine the sixth degree of freedom (roll) if the two sensors are positioned relative to each other in a known configuration. An advantage of using two sensors to provide six degrees of positioning and orientation, rather than a single six DOF sensor is that the two sensors (in and of themselves that are less than six DOF) may each might be smaller than a six DOF sensor. Furthermore, if it is desired to have the main lumen have its center near the center of the catheter, a large single sensor might force the main lumen to be smaller than what two smaller sensors positioned at two different places around the main lumen might require.

An advantage of electrode-based sensing is that the electrodes can be used for other purposes (pacing, ECG sensing) and can the same setup can be used to determine the position of any catheter electrodes in the body. Electromagnetic sensors may be more accurate and precise than a simple electrode.

The addition of a pose sensor to a mechanical scanned imaging catheter has several advantages. It makes it easier for the user to understand the relationship of the maneuvers applied to the catheter (made by the user or an actuator such as a robotic mechanism outside of the body) to the position and orientation relative to the reference frame. It allows the imaging data to be mapped to a 3D or 4D (3D+time, such as ECG-gated time windows) dataset and if Doppler is enabled, a 5D dataset (3D+time+flow). Furthermore, image quality with imaging catheters is dependent on several aspects of the catheter. Imaging data acquired within a preferred region where the imaging beams are more focused, such as in the near field of a single element of a single element ultrasound transducer (as opposed to an array transducer) generally has better quality than imaging data outside of that region. Therefore, by moving the distal portion of the imaging catheter within the body, some imaging data will be of better quality as the catheter moves closer to the tissue of interest.

In one example embodiment, 3D or 4D imaging data that was acquired outside of the preferred region can be updated with the imaging data that is later acquired within a preferred or optimal region to improve the overall quality of the dataset.

Furthermore, ultrasound image quality can be somewhat dependent on the angle of incidence between the ultrasound beam and the structures imaged. Therefore, in some example embodiments, images may be obtained of the same structure from multiple viewpoints, and the approximate angle of incidence may be estimated using segmentation algorithms known in the art. For example, often optimal imaging signal is at normal incidence. In some cases, at normal incidence, reverberation artifacts are present and it is preferred to be near normal incidence, but off by a small amount (approximately 3-10 degrees). The imaging data that was collected with the most preferred angles of incidence may be employed to create the 3D or 4D composite imaging data sets.

Furthermore, ultrasound image quality can be somewhat dependent on the distance between the ultrasound transducer and the structures being imaged. For example, if the transducer is a focused transducer, optimal imaging will occur within the focal region. The focal region is often defined as the full width half maximum (FWHM) region along the depth direction along a given A-scan line. In the case of an unfocused transducer, the acoustic beam. Approximate distance may be estimated using segmentation algorithms known in the art. The imaging data that was collected with the most preferred distance may be employed to create the 3D or 4D composite imaging data sets.

Figure 10:
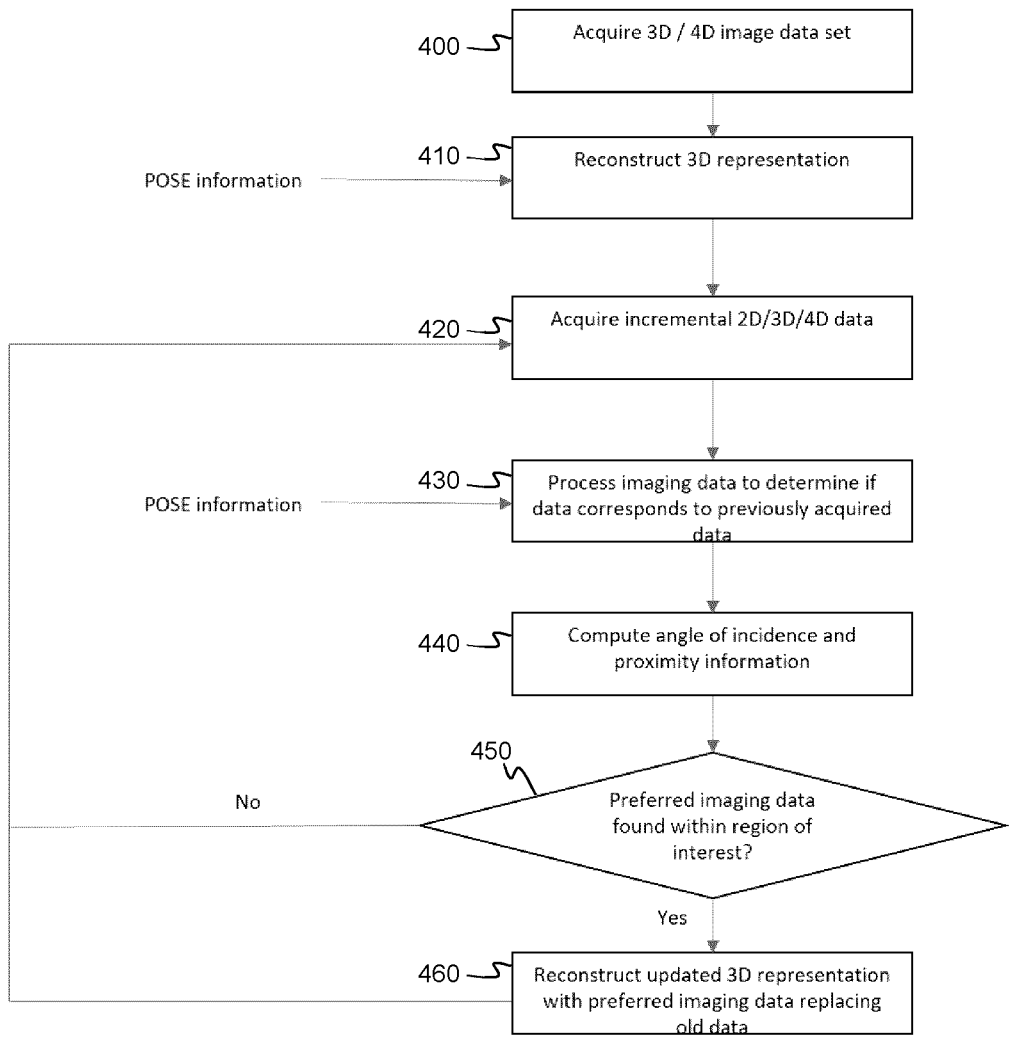
FIG. 10 is a flow chart illustrating an example method in which the computed angle of incidence and/or proximity associated with image data is employed to selectively update a 3D image.

Referring now to FIG. 10, a flow chart is shown the illustrates such an example method, in which the computed angle of incidence and/or proximity associated with image data is employed to selectively update a 3D image. A 3D or 4D image data set is initially acquired, as shown at 400, and a 3D representation is reconstructed from the data set, as shown at 410, using information provided by the POSE sensor. Additional incremental imaging data is then acquired, which may be 2D, 3D or 4D, as shown at 420. Using POSE information, the incremental image data is processed to determine if it corresponds, at least in part, to previously acquired image data, as shown at 430. The POSE information is then employed to determine, at step 440 an angle of incidence and/or proximity information associated with the incremental imaging data. A determination is then made at step 450 whether or not the incremental imaging data, with its associated angle of incidence and/or proximity information, represents preferred imaging data (e.g. based on pre-selected threshold values, or, for example, based on a comparison with a look-up table containing preferred ranges). In the absence of the identification of preferred imaging data, steps 420-440 may optionally be repeated. If preferred imaging data is identified, the 3D representation may be reconstructed using the preferred imaging data, as shown at 460.

Generally, in the field of minimally invasive imaging probes, the insertable portion is configured to be flexible, especially when advanced into the vasculature, which has some tortuosity to it. Accordingly, if the rigid reinforcement member 180 is too long, it will make produce local stiffness that is undesirable. In some example embodiments, the length of the rigid member may be less than 20 times the outer diameter of the probe, less than 10 times the outer diameter of the probe, less than 5 times the outer diameter of the probe, less than 3 times the outer diameter of the probe or less than 1 times the outer diameter of the probe.

Figure 8:
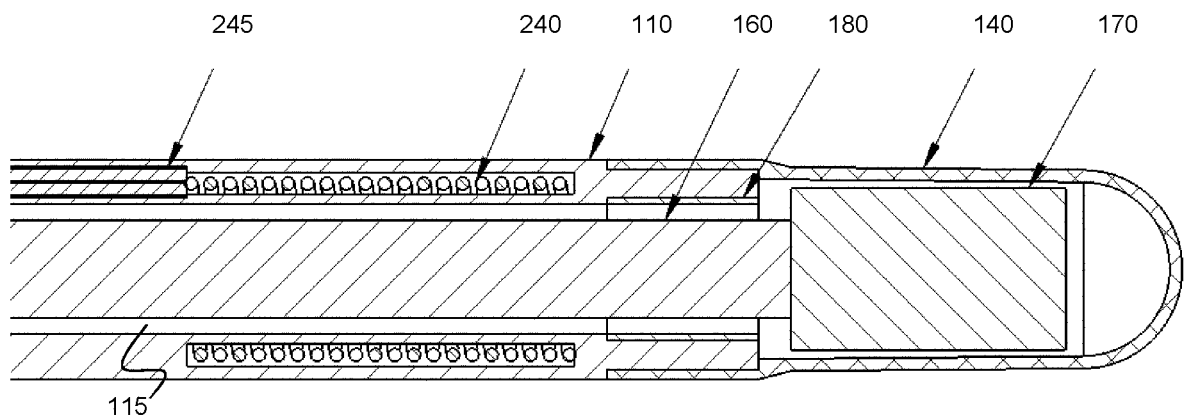
FIG. 8 illustrates an example embodiment of an imaging probe in which the radial extent of a distal imaging assembly is larger than the inner radius of the elongate proximal sheath, and wherein the elongate proximal sheath includes a conductive wiring.

FIG. 8 shows an example embodiment in which the distal region of a catheter sheath incorporates a winding 240 that surrounds the main lumen. The winding may be in electrical communication with external electronics via electrically conductive conduits 245.

The example winding shown in FIG. 8 could be used for several applications, such as, but not limited to:
1) acting as a POSE sensor or emitter;
2) creating a local magnetic field to actuate a motion within the catheter;
3) creating a local magnetic field to attract a magnetic component outside of the catheter; and
4) generally sensing electromagnetic signals within the body, including those that might have introduced artifacts into the imaging signal from the imaging assembly.

A potential advantage of providing a POSE sensor that surrounds the main lumen 115 (as in FIG. 8) as opposed to adjacent to the main lumen 115 (as in FIG. 6A) is that it such a configuration may accommodate a larger main lumen than the embodiment of FIG. 6A, and may enable a more radially symmetric design.

Figure 9:
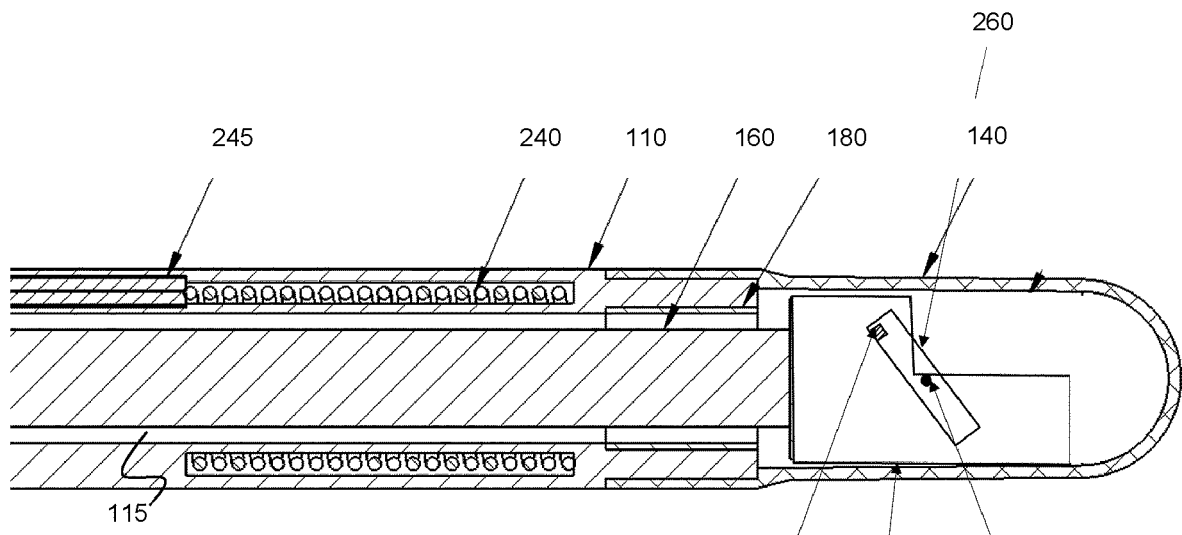
FIG. 9 illustrates an example embodiment of an imaging probe in which the radial extent of a distal imaging assembly is larger than the inner radius of the elongate proximal sheath, and wherein the elongate proximal sheath includes a conductive wiring that can is capable of generating a magnetic field to actuate a tiltable transducer having a magnet attached thereto.

An example implementation in which the winding 240 is capable of actuating motion within the probe involves the incorporation of a magnet within the backing of a tiltable transducer. An example of such an embodiment is shown in FIG. 9, where the tiltable transducer 260 tilts around a pivot axis 265 and is pivotally mounted to a shell 270, where the tiltable transducer 260 has a magnet 280 attached thereto, recessed therein, or otherwise mechanically supported. The ultrasound transducer 260 is connected via conductive springs (not shown) to one or more electrical signal conduits (not shown) within the torque cable. By applying a current to the winding 240 through proximal winding conductors 245, a magnetic field can be generated that tilts tiltable transducer 260 via attractive/repelling forces between the transducer magnet 280 and the winding 240. In other example embodiments, the magnet 280 does not need to necessarily be attached directly to the transducer 260. For example, the magnet could be attached to a push rod or shaft to cause a transducer within the imaging assembly to tilt or translate.

The winding conduits 245 are typically electrically insulated from each other and, either supplied with insulation or insulated as a result of their incorporation into the catheter wall. The winding conduits 245 could be incorporated into a reinforcement braiding in the sheath to reduce the use of cross-sectional area along the main portion of the sheath.

In another example embodiment, the distal tip region may be configured to include multiple transducers supported by one or more imaging assemblies, where the imaging assemblies and/or transducers have a lateral extent that is larger than the inner diameter of the main lumen of the catheter.

Although the preceding example embodiments have illustrated various aspects of the present disclosure through examples involving an imaging probe/catheter having an imaging assembly, it will be understood that the example embodiments disclosed herein may be adapted for use with medical probes having non-imaging rotatable devices in alternative to, or in additional to, an imaging assembly.

It will be understood that the distal tip described and shown herein, which includes a distal dome-shaped profile, provides a non-limiting example of a distal tip configuration, and that other distal tip geometries and profiles may be employed without departing from the intended scope of the present disclosure. Furthermore, although the preceding example embodiments show closed distal tips, it will be understood that the distal tip may include one or more openings or ports.

Figure 11:
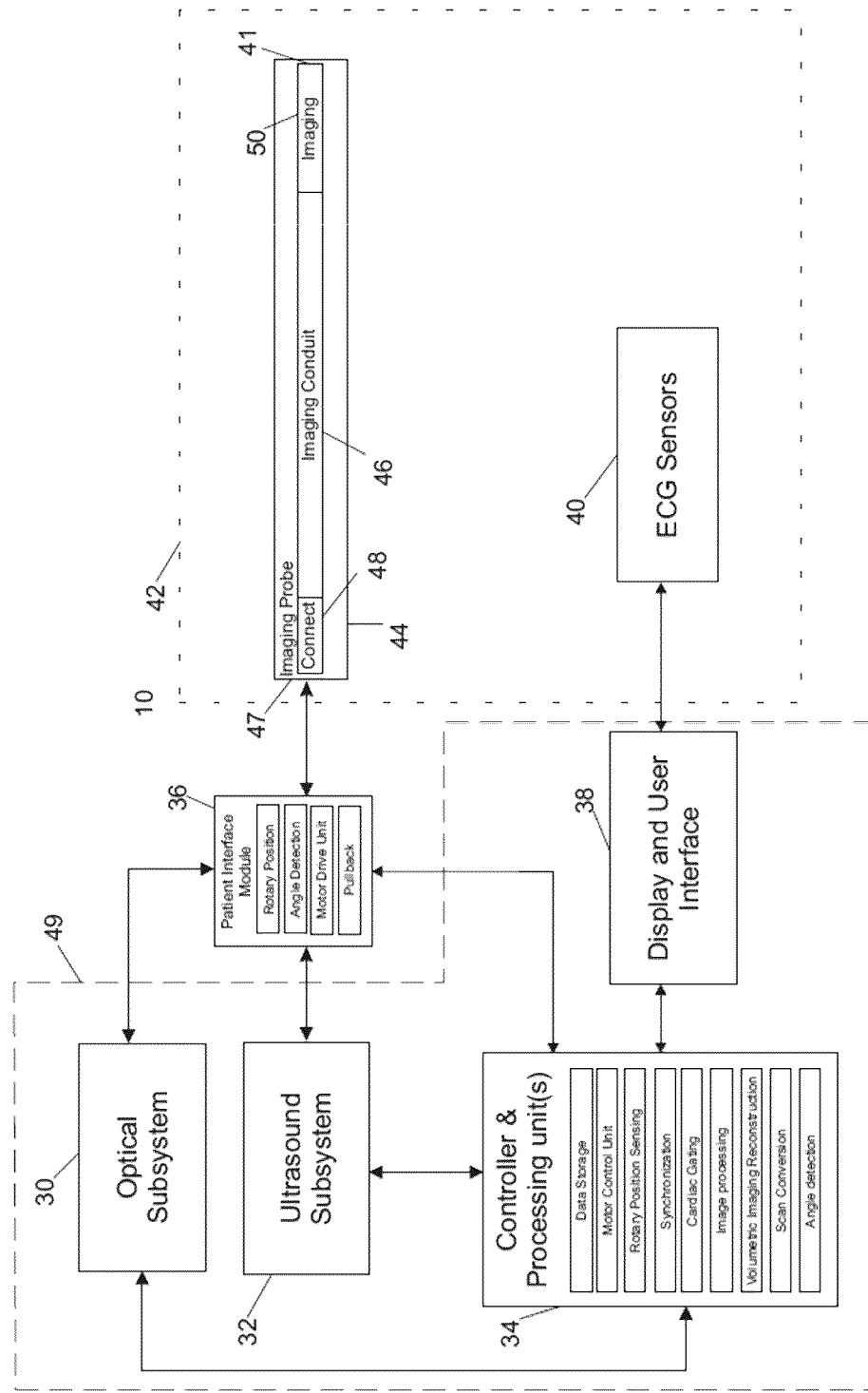
FIG. 11 is a schematic of an example imaging system for either ultrasound imaging, optical imaging or both.

Referring now to FIG. 11, an imaging system is shown at 10 comprising imaging probe 44, which connects via patient interface module 36 to image processing and display system 49. Image processing and display system 49 includes hardware to support one or more imaging modalities, such as ultrasound, optical coherence tomography, angioscopy, infrared imaging, near infrared imaging, Raman spectroscopy-based imaging, or fluorescence imaging. Specific embodiments of ultrasonic imaging probes and combined ultrasonic and optical imaging probes are disclosed by Courtney et al. in US Patent Publication No. 20080177183, titled "Imaging Probe with Combined Ultrasounds and Optical Means of Imaging" and filed on Jan. 22, 2008, US Patent Publication No. 20080177138, titled "Scanning Mechanisms for Imaging Probe" and filed on Jan. 22, 2008 and US Patent Publication No. 20090264768, titled "Scanning Mechanisms for Imaging Probe" and filed on Mar. 27, 2009, each of which are incorporated herein by reference in their entirety.

Controller and processing unit 34 is employed to facilitate the coordinated activity of the many functional units of the system, and may contain some or all of the components shown in the Figure and listed herein. Controller and processing unit 34, or a separate computing device or system, may also be employed to implement the methods associated with the flow chart shown in FIG. 10. An operator interacts with system 50 via display and/or user interface 38. System 10 may further include electrode sensors 40 to acquire electrocardiogram signals from the body of the patient being imaged. The electrocardiogram signals may be used to time the acquisition of imaging data in situations where cardiac motion may have an impact on image quality. The electrocardiogram may also serve as a trigger for when to begin an acquisition sequence, such as when to begin changing the speed of rotation of a motor in order to cause a desired scan pattern to take effect. For example, electrocardiogram triggered initiation of an imaging sequence may enable images to be acquired during a particular phase of the cardiac cycle, such as systole or diastole. Optical subsystem 30, if included in a particular implementation of an imaging system, may include any or all of the following components: interferometer components, one or more optical reference arms, optical multiplexors, optical demultiplexers, light sources, photodetectors, spectrometers, polarization filters, polarization controllers, timing circuitry, analog to digital converters, parallel processing arrays and other components known to facilitate any of the optical imaging techniques. Ultrasound subsystem 32 may include any or all of the following components: pulse generators, electronic filters, analog to digital converters, parallel processing arrays, envelope detectors, amplifiers including time gain compensation amplifiers and other components known to facilitate acoustic imaging techniques.

Controller and processing units 34, if included in a particular implementation of the imaging system, serve multiple purposes. Those skilled in the art will appreciate that specific components required depend on the needs of a particular type of imaging system. For example, controller and processing units may include any combination of a motor drive controller, data storage components (such as memory, hard drives, removable storage devices, readers and recorders for media such as CDs, DVDs, and Bluray™ discs), position sensing circuitry and/or software, angle detection circuitry and/or software, timing circuitry and/or software, cardiac gating functionality, volumetric imaging processors, scan converters and others. As noted above, display and user interface 38 is also optionally provided for either real time display or display of data at a time later than the time at which imaging data is acquired.

It is to be understood that patient interface module 36 and controller and processing units 34 are but one example illustration of the selection and organization of hardware subsystems, and that many other implementations are possible. For example, patient interface module 36 may be housed with controller and processing units 34 within processing and display system 49.

Example imaging probe 44 includes an imaging assembly 50, optional imaging conduit 46 along a substantial portion of its length, and connector 48 at its proximal end 47. Imaging assembly 50 is located near distal end 41 of imaging probe 44. Imaging assembly 50 generally refers to the components of the imaging probe 44 from which the signals (either acoustic, optical or both) are collected for the purposes of imaging a region that is proximate to imaging assembly 50. Imaging assembly 50 may house transducers for transmitting and/or receiving imaging radiation. The emitter and receiver may be a single component, as is often the case with a piezoelectric transducer.

In the case of optical imaging, imaging assembly 50 typically contains the distal tip of a fiber optic, as well as a combination of optical components such as a lens (for instance, a ball lens or a GRIN lens). A mirror and/or prism may be included for use in beam delivery and/or collection. Optionally, there may be an optical detector, such as a CCD array, or an optical light source, such as one or more LEDs, incorporated directly in the imaging assembly that may obviate the need for one or more fiber optics in an optical imaging probe. Imaging probe 44 may contain ports at one or more points along its length to facilitate flushing. Moreover, imaging assembly 50, connector 48 and/or imaging conduit 46 may be filled and/or surrounded with a fluid such as saline, and may be flushed. In applications involving optical imaging, imaging probe 44 may be filled with a gas. The gas may include carbon dioxide or another readily dissolved gas with minimal biotoxicity. Alternatively, in the case of a multimodal optical/acoustic imaging system, imaging assembly 50 may be compartmentalized to include at least one gas-filled compartment or lumen for optical imaging and at least one fluid filled compartment or chamber for acoustic imaging.

Imaging conduit 46 includes at least one conductive wire (optionally two or more) that connect an emitter and/or receiver via connection to an adapter, herein referred to as patient interface module 36. Imaging conduit 46 may include a fiber optic, for example, wrapped by two layers of electrical wire that are electrically insulated from one another. Imaging conduit 46 may further be reinforced by other structural features, such as helically wrapped wires or other designs used to construct imaging torque cables for rotating scan mechanisms. Alternatively, imaging conduit 46 may contain electrical conductors, and a rotational mechanism may be located remote from the proximal end for imparting rotary motion to the imaging assembly. One example mechanism includes a micro-motor and a slip ring in close proximity to the imaging assembly.

The imaging probe 44 may optionally include memory, such as an EEPROM for storing information including calibration information, serial information, probe design information, desired filter information, and any other probe specific information. This memory may reside in connector 48.

Patient interface module 36 facilitates transmission of signals within any fibers and/or wires to the appropriate image processing units. It may contain a motor drive unit for imparting rotational motion to the components of the imaging mechanism. Additional sensors may be incorporated as part of patient interface module 36, such as position sensing circuitry, for example, to sense the angle of rotation of a rotary component within the imaging probe 44 and/or for detecting the angle of deflection of a member at the distal end 41 of the imaging probe 44. Additionally, patient interface module 36 may include amplifiers to improve the transmission of electrical signals or power between the imaging probe 44 and the rest of the system.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

Therefore what is claimed is:

1. A method of assembling an imaging probe, the method comprising:
   providing an elongate sheath having an inner lumen and a distal opening;
   securing a rigid reinforcing member within the elongate sheath such that the rigid reinforcing member contacts an inner surface of the elongate sheath or is embedded within the elongate sheath, and such that the rigid reinforcing member extends longitudinally within said elongate sheath to define a distal reinforcement region of the elongate sheath;
   providing a rotatable imaging conduit and an imaging assembly, wherein the imaging assembly is connected to a distal end of the rotatable imaging conduit, and wherein a lateral extent of the imaging assembly is larger than a diameter of the inner lumen of the elongate sheath;
   inserting the rotatable imaging conduit through the distal opening of the elongate sheath such that the imaging assembly resides beyond a distal end of the elongate sheath;
   providing a distal tip having a distal end and an open proximal end;
   positioning the distal tip over the imaging assembly such that a proximal portion of the distal tip contacts and overlaps with the elongate sheath over a distal contact region of the elongate sheath, the distal contact region residing within the distal reinforcement region without extending beyond the distal reinforcement region, such that within a full longitudinal extent of the distal contact region, the elongate sheath resides radially between the proximal portion of the distal tip and at least a portion of the rigid reinforcing member; and
   bonding the distal tip to the elongate sheath, wherein the bonding is performed via a local application of heat, and wherein the rigid reinforcing member provides structural reinforcement to the elongate sheath and avoids deformation of the elongate sheath during the local application of heat.

2. The method according to claim 1 wherein the rigid reinforcing member extends in a distal direction beyond the distal end of the elongate sheath.

3. The method according to claim 1 wherein the distal tip is bonded to the elongate sheath via laser welding.

4. The method according to claim 3 wherein an optical absorbing medium is placed between the proximal portion of the distal tip and the elongate sheath.

5. An imaging probe comprising:
   an elongate sheath having an inner lumen and a distal opening;
   a rigid reinforcing member residing within said elongate sheath such that said rigid reinforcing member contacts an inner surface of said elongate sheath or is embedded within said elongate sheath, and such that said rigid reinforcing member extends longitudinally within said elongate sheath to define a distal reinforcement region of said elongate sheath;
   a rotatable conduit extending through said inner lumen;
   an imaging assembly having a lateral extent exceeding a diameter of the inner lumen of said elongate sheath, wherein said imaging assembly is connected to a distal end of said rotatable conduit such that said imaging assembly resides beyond a distal end of said elongate sheath; and
   a distal tip housing said imaging assembly, wherein a proximal portion of said distal tip is bonded to and overlaps with said elongate sheath over a distal contact region of the elongate sheath, the distal contact region residing within the distal reinforcement region without extending beyond the distal reinforcement region, such that within a full longitudinal extent of the distal contact region, said elongate sheath resides radially between said proximal portion of said distal tip and at least a portion of said rigid reinforcing member;

wherein said rigid reinforcing member provides structural reinforcement to said elongate sheath and avoids deformation of said elongate sheath when said distal tip is bonded to said elongate sheath via a local application of heat.

6. The imaging probe according to claim 5 wherein said rigid reinforcing member is a pull ring for a deflection mechanism.

7. The imaging probe according to claim 5 wherein said rigid reinforcing member is a marker band.

8. The imaging probe according to claim 5 wherein said elongate sheath comprises a plurality of side lumens.

9. The imaging probe according to claim 8 wherein one or more of said side lumens comprise at least a portion of a sensing mechanism.

10. The imaging probe according to claim 8 wherein one or more of said side lumens comprises a pose sensor.

11. The imaging probe according to claim 5 wherein a longitudinal extent of said rigid reinforcing member is less than an outer diameter of said imaging probe.

* * * * *